(12) United States Patent
Yan et al.

(10) Patent No.: US 11,883,684 B2
(45) Date of Patent: Jan. 30, 2024

(54) IMAGE-GUIDED METHOD, RADIO THERAPY DEVICE, AND COMPUTER STORAGE MEDIUM

(71) Applicant: OUR UNITED CORPORATION, Xi'an (CN)

(72) Inventors: Hao Yan, Xi'an (CN); Jiuliang Li, Xi'an (CN); Chun Luo, Xi'an (CN); Zhongya Wang, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 300 days.

(21) Appl. No.: 17/160,959

(22) Filed: Jan. 28, 2021

(65) Prior Publication Data

US 2021/0252309 A1    Aug. 19, 2021

Related U.S. Application Data

(63) Continuation of application No. PCT/CN2020/075410, filed on Feb. 14, 2020.

(51) Int. Cl.
*G06T 7/20* (2017.01)
*G06T 7/30* (2017.01)
(Continued)

(52) U.S. Cl.
CPC ......... *A61N 5/1039* (2013.01); *A61N 5/1049* (2013.01); *G06T 7/0012* (2013.01);
(Continued)

(58) Field of Classification Search
CPC ............... A61N 5/1039; A61N 5/1049; A61N 2005/1062; G06T 7/0012; G06T 7/20;
(Continued)

(56) References Cited

U.S. PATENT DOCUMENTS

2003/0151720 A1    8/2003  Chernyak et al.
2006/0291621 A1   12/2006  Yan et al.
(Continued)

FOREIGN PATENT DOCUMENTS

CN    105139442    12/2015
CN    106023140    10/2016
(Continued)

*Primary Examiner* — Siamak Harandi
(74) *Attorney, Agent, or Firm* — Emerson, Thomson & Bennett, LLC; Roger D. Emerson; Matt J. Wilson

(57) ABSTRACT

An image-guided method and radio therapy device are provided. The method includes: acquiring a rotation offset, a planned image and a real-time image of a target object; and determining a tracking offset based on the rotation offset, the planned image and the real-time image, the tracking offset being used for tracking the target object; where the rotation offset is generated by a position difference of the target object in a planning stage and a treatment stage. The planned image of the target object is acquired in the planning stage. The tracking offset is determined based on the rotation offset, the planned image and the real-time image. The tracking of the target object based on the tracking offset compensates for image distortion caused by the deflection of the position of the target object in the planning stage and the treatment stage.

20 Claims, 3 Drawing Sheets

(51) Int. Cl.
*G06T 7/70* (2017.01)
*A61N 5/10* (2006.01)
*G06T 11/00* (2006.01)
*G06T 7/00* (2017.01)

(52) U.S. Cl.
CPC .................. *G06T 7/20* (2013.01); *G06T 7/30* (2017.01); *G06T 7/70* (2017.01); *G06T 11/005* (2013.01); *G06T 2207/10081* (2013.01); *G06T 2207/30004* (2013.01)

(58) Field of Classification Search
CPC . G06T 7/30; G06T 7/70; G06T 11/005; G06T 2207/10081; G06T 2207/30004
See application file for complete search history.

(56) References Cited

U.S. PATENT DOCUMENTS

| | | | |
|---|---|---|---|
| 2008/0130825 A1 | 6/2008 | Fu et al. | |
| 2017/0165008 A1 | 6/2017 | Finley | |
| 2018/0056090 A1* | 3/2018 | Jordan | A61N 5/103 |
| 2018/0197303 A1 | 7/2018 | Jordan et al. | |
| 2018/0229056 A1* | 8/2018 | Paysan | A61N 5/1081 |
| 2019/0046232 A1 | 2/2019 | Tokuda et al. | |

FOREIGN PATENT DOCUMENTS

| | | |
|---|---|---|
| CN | 106408509 A | 2/2017 |
| CN | 107669284 | 2/2018 |
| CN | 108744313 A | 11/2018 |
| CN | 108815719 | 11/2018 |
| CN | 110292723 A | 10/2019 |
| CN | 110366439 A | 10/2019 |
| FR | 2797978 A1 | 3/2001 |
| JP | 2010075551 A | 4/2010 |
| WO | WO2015125600 A1 | 8/2015 |
| WO | WO2015136392 A1 | 9/2015 |
| WO | WO2018007518 A1 | 1/2018 |
| WO | WO2019140853 A1 | 7/2019 |
| WO | WO2020029304 A1 | 2/2020 |

* cited by examiner

IMAGE-GUIDED METHOD, RADIO THERAPY DEVICE, AND COMPUTER STORAGE MEDIUM

CROSS REFERENCE TO RELATED APPLICATIONS

The present application is a continuation of international application PCT/CN2020/075410 filed on Feb. 14, 2020, and entitled "IMAGE-GUIDED METHOD, RADIO THERAPY DEVICE, AND COMPUTER STORAGE MEDIUM", which is hereby incorporated by reference in its entireties.

TECHNICAL FIELD

Embodiments of the present disclosure relate to the field of radio therapy, and especially to, an image-guided method, apparatus, radio therapy device, and computer storage medium.

BACKGROUND

Radiotherapy is a method for treating a tumor using radioactive rays. As one of the main means for treating malignant tumors, radiotherapy can cause complete necrosis or apoptosis of cancer cells.

One of the key technologies of radiotherapy is to maintain precise positioning of the tumor during treatment. Before radiotherapy is performed on a patient, the patient needs to be positioned based on a planned image before the treatment of the patient, such that a target object is aligned with an isocenter point of a radio therapy device.

Since the planned image before the treatment is generally generated using a diagnostic imaging device, e.g., CT, MRI, or PET, the patient is positioned using the radio therapy device. Therefore, when the patient lies on two different devices, a body position may change in a six-dimensional direction (three translational directions of X, Y, and Z, and three rotational directions around X, Y, and Z axes). Thus, it is necessary to compensate for the six-dimensional offset by moving a treatment couch to complete positioning of the patient.

However, when a three-dimensional treatment couch (i.e., the treatment couch can move only in the three translational directions of X, Y, and Z) is used as a treatment couch, a rotation offset caused by a position difference will not be compensated for. Thus, if a registration is performed between a target area image of the patient and the planned image before the treatment during real-time image guidance, the registration accuracy will be reduced, thereby affecting the treatment effect.

SUMMARY

In view of this, one of the technical problems to be solved by embodiments of the present disclosure is to provide an image-guided method, apparatus, radio therapy device, and computer storage medium, to overcome the defects of existing technologies failing to compensate for a rotation offset in a positioning stage, thereby resulting in reduced registration accuracy between a target area during treatment and an image before treatment of a patient, and affecting the treatment accuracy of the patient.

In a first aspect, an embodiment of the present disclosure provides an image-guided method, including: acquiring a rotation offset, a planned image, and a real-time image of a target object, the rotation offset being generated by a position difference of the target object in a planning stage and a treatment stage; and determining a tracking offset based on the rotation offset, the planned image, and the real-time image, the tracking offset being used for tracking the target object.

Alternatively, in an embodiment of the present disclosure, the rotation offset is a positioning rotation offset, and the positioning rotation offset is a rotation offset of the target object determined in a positioning stage.

Alternatively, in an embodiment of the present disclosure, the determining the positioning rotation offset of the target object includes:
  acquiring the planned image and a positioning image of the target object; and
  determining the positioning rotation offset based on the planned image and the positioning image.

Alternatively, in an embodiment of the present disclosure, the determining the tracking offset based on the rotation offset, the planned image, and the real-time image includes:
  determining a reconstructed compensation image based on the rotation offset and the planned image; and
  registering the reconstructed compensation image with the real-time image to determine the tracking offset.

Alternatively, in an embodiment of the present disclosure, the determining the reconstructed compensation image based on the rotation offset and the planned image includes:
  compensating for the planned image based on the rotation offset to obtain a compensated planned image; and
  reconstructing the compensated planned image at a first angle and a second angle respectively, to obtain two reconstructed compensation images corresponding to the first angle and the second angle.

Alternatively, in an embodiment of the present disclosure, the determining the reconstructed compensation image based on the rotation offset and the planned image includes:
  reconstructing the planned image at the first angle and the second angle respectively, to obtain two reconstructed images corresponding to the first angle and the second angle; and
  compensating for the two reconstructed images corresponding to the first angle and the second angle respectively based on the rotation offset, to obtain two reconstructed compensation images corresponding to the first angle and the second angle.

Alternatively, in an embodiment of the present disclosure, the registering the reconstructed compensation image with the real-time image to determine the tracking offset includes:
  registering the two reconstructed compensation images with the two real-time images respectively to obtain two first offsets, where the two real-time images are obtained by imaging the target object at the first angle and the second angle respectively; and
  computing the tracking offset based on the two first offsets.

Alternatively, in an embodiment of the present disclosure, the determining the tracking offset based on the rotation offset, the planned image, and the real-time image includes:
  compensating for two real-time images based on the rotation offset to obtain two compensated real-time images, the two real-time images being obtained by imaging the target object at a third angle and a fourth angle respectively;
  reconstructing the planned image at the third angle and the fourth angle respectively to obtain two reconstructed images corresponding to the third angle and the fourth angle; and registering the two compensated real-time images with the two reconstructed images to determine the tracking offset.

Alternatively, in an embodiment of the present disclosure, the determining the positioning rotation offset based on the planned image and the positioning image includes:

reconstructing N positioning images to obtain a three-dimensional image, the N positioning images being obtained by imaging the target object at N different shooting angles respectively, the N being a natural number greater than 2; and registering the three-dimensional image with the planned image to obtain the positioning rotation offset.

Alternatively, in an embodiment of the present disclosure, the determining the positioning rotation offset based on the planned image and the positioning image includes:

reconstructing the planned image at two orthogonal shooting angles respectively, to obtain two reconstructed images corresponding to the two orthogonal shooting angles;

registering two positioning images with the two reconstructed images to obtain two second offsets, the two positioning images being obtained by imaging the target object at the two orthogonal shooting angles respectively; and computing the positioning rotation offset based on the two second offsets.

In a second aspect, an embodiment of the present disclosure provides an image-guided apparatus, including:

an acquiring module configured to acquire a rotation offset, a planned image, and a real-time image of a target object; and a determining module configured to determine a tracking offset based on the rotation offset, the planned image, and the real-time image, the tracking offset being used for tracking the target object;

where the rotation offset is generated by a position difference of the target object in a planning stage and a treatment stage.

In a third aspect, an embodiment of the present disclosure provides a radio therapy device, including: a processor and a memory, the memory storing program instructions, the processor being configured to invoke the program instructions in the memory to execute the method according to the first aspect or any one embodiment of the first aspect.

In a fourth aspect, an embodiment of the present disclosure provides a computer storage medium, storing a computer program, where the computer program, when executed by a processor, implements the method according to the first aspect or any one embodiment of the first aspect.

Embodiments of the present disclosure provide an image-guided method, apparatus, radio therapy device, and computer storage medium. The image-guided method includes: acquiring a rotation offset, a planned image, and a real-time image of a target object; and determining a tracking offset based on the rotation offset, the planned image, and the real-time image, the tracking offset being used for tracking the target object; where the rotation offset is generated by a position difference of the target object in a planning stage and a treatment stage. The planned image of the target object is acquired in the planning stage. Because a position of the target object will deflect in the planning stage and the treatment stage, the tracking offset is determined based on the rotation offset, the planned image, and the real-time image, such that the tracking of the target object based on the tracking offset in the treatment stage of a patient can compensate for image distortion caused by target area deflection, and improve the registration accuracy of a target area and the planned image before the treatment of the patient, thereby improving the treatment accuracy of the patient.

BRIEF DESCRIPTION OF THE DRAWINGS

Some specific embodiments of embodiments of the present disclosure will be described in detail below with reference to the accompanying drawings in an example manner, instead of a limiting manner. Identical reference numerals in the accompanying drawings represent identical or similar components or parts. Those skilled in the art should understand that these accompanying drawings may not be drawn to scale. In the figures.

DETAILED DESCRIPTION

Any technical solution in embodiments of the present disclosure may not necessarily be implemented to achieve all the above advantages.

To enable those skilled in the art to better understand the technical solutions in the embodiments of the present disclosure, the technical solutions in the embodiments of the present disclosure will be clearly and completely described below with reference to the accompanying drawings in the embodiments of the present disclosure. Apparently, the described embodiments are merely a part, instead of all, of the embodiments of the present disclosure. All other embodiments obtained by those of ordinary skills in the art based on the embodiments of the present disclosure should fall within the scope of protection of the embodiments of the present disclosure.

It should be noted that an object in the present disclosure is only to express a singular concept, and neither is used for limitation, nor refers in particular to a certain one. For example, the target object refers to an object, and may be any one object. The "first, second, third, and fourth" in the present disclosure are only used for distinguishing between names, and neither represent a sequential relationship, nor can be understood as indicating or implying relative importance or implicitly indicating the number of indicated technical features. For example, the first offset is an offset obtained by registering a reconstructed compensation image with a real-time image, while the second offset is an offset obtained by registering a positioning image with a reconstructed image. For another example, the first angle and the second angle are used for representing two different shooting angles, while the third angle and the fourth angle are used for representing two different shooting angles, where values of the first angle, the second angle, the third angle, and the fourth angle do not affect each other, as long as the first angle is different from the second angle, and the third angle is different from the fourth angle.

Specific implementations of embodiments of the present disclosure will be further described below with reference to the embodiments and the accompanying drawings of the present disclosure.

Embodiment I

Figure 1:
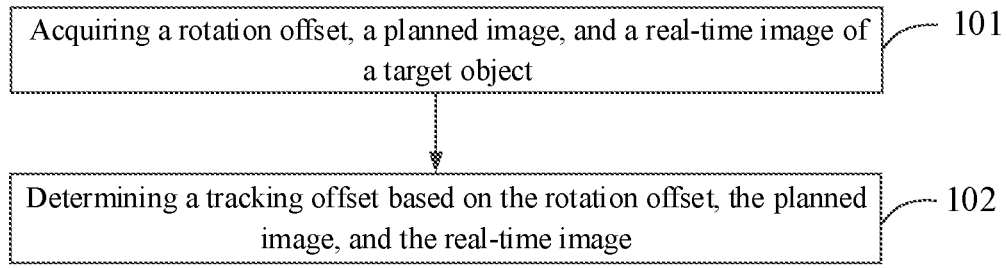
FIG. 1 is a schematic flowchart of an image-guided method provided in an embodiment of the present disclosure.

FIG. 1 is a schematic flowchart of an image-guided method according to an embodiment of the present disclosure. The image-guided method can be applied to a medical device. Here, the medical device in embodiments of the present disclosure is described using a radio therapy device as an example. The radio therapy device may include, but is not limited to, a patient fixing structure and at least one imaging apparatus. The radio therapy device can control movement of the patient fixing structure, such that a patient moves with the patient fixing structure, and the imaging apparatus can rotate around the patient fixing structure. The imaging apparatus in the embodiments of the present disclosure includes: a x-ray tube and a detector which are oppositely arranged, and can take a medical image of the patient on the patient fixing structure at a preset shooting angle as required. X-rays emitted from the x-ray tube can be received by the detector after passing through a target area of the patient, thus forming a positioning image of the patient or a real-time image of the patient. The imaging apparatus may also be an imaging structure for other types of medical images, such as: magnetic resonance imaging (MRI for short), or positron emission computed tomography (PET for short). For example, when the radio therapy device includes a patient fixing structure and an imaging apparatus. The imaging apparatus can rotate around the patient fixing structure to the preset shooting angle to radiograph an affected part of the patient on the patient fixing structure. For another example, when the radio therapy device includes a patient fixing structure and at least two imaging apparatuses, in an application scenario, one of the imaging apparatuses is fixedly arranged at a shooting angle with respect to the patient fixing structure, while the other imaging apparatus can rotate around the patient fixing structure, to radiograph the affected part of the patient on the patient fixing structure at any shooting angle; in another application scenario, either of the two imaging apparatuses rotates around the patient fixing structure, and can radiograph the affected part of the patient on the patient fixing structure at any shooting angle; and in still another application scenario, either of the two imaging apparatuses is fixedly arranged around the patient fixing structure, and can radiograph the affected part of the patient on the patient fixing structure only at a fixed shooting angle. The shooting angle may be expressed as an angle value representing an azimuth in a planar polar coordinate system, and the origin is a point around which the imaging apparatus rotates.

In an application scenario, the image-guided method may be installed on the medical device (e.g., the radio therapy device, the imaging apparatus, or an operating table) in the form of software, thus achieving an image-guided process in a medical activity. In another application scenario, an executing body of the image-guided method may be, e.g., a controller of the radio therapy device, a processor of the radio therapy device, a control structure connected to the radio therapy device, or a server connected to the radio therapy device. This is not limited in the present disclosure.

The image-guided method provided in the present disclosure can be applied to any one image-guided medical activity, such as image-guided radio therapy (IGRT), an intracranial tumor resection, or other related image-guided surgical operations. As shown in FIG. 1, the image-guided method includes the following steps:

Step 101: acquiring a rotation offset, a planned image, and a real-time image of a target object.

The rotation offset is generated by a position difference of the target object in a planning stage and a treatment stage.

Figure 2:
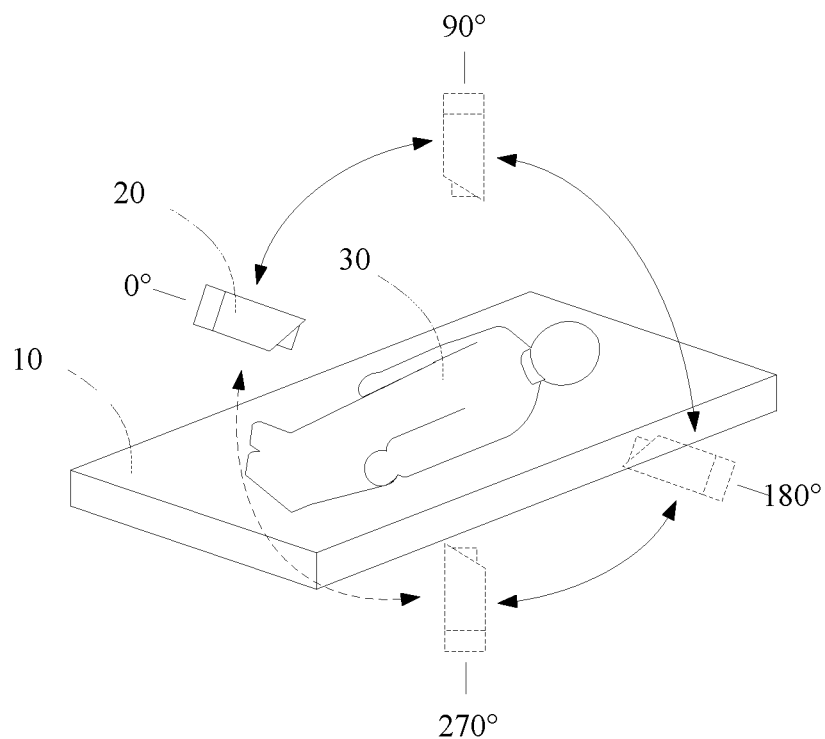
FIG. 2 is an application scenario of the image-guided method provided in an embodiment of the present disclosure.

It should be noted that the target object of the present disclosure is used for denoting an affected part or a target area of a patient. The affected part of the patient may be located in his head such as an intracranial tumor, or in his body such as a lung tumor. The target object is denoted, e.g., as the target area of the patient in embodiments of the present disclosure. It is understandable that the patient refers to a subject on which these medical activities are implemented, e.g., a patient requiring radiotherapy or surgery, but is not limited to a sick person. The imaging apparatus rotates around the patient fixing structure, and can obtain an image of the target object by radiographing the patient on the patient fixing structure at a few shooting angles. In an application scenario shown in FIG. 2, FIG. 2 is an application scenario of an image-guided method provided in an embodiment of the present disclosure. FIG. 2 shows an imaging apparatus rotatable within a range of 360 degrees, namely, leftward, upward, rightward, and downward, of a patient, and a plane of a rotation trajectory of the imaging apparatus may be, but is not limited to, a vertical plane, a horizontal plane, an inclined plane, and other planes. In the present disclosure, an angle between a ray in a shooting direction and a ray from a left side to a right side of the patient is used as a shooting angle. Of course, the shooting angle may also have other definitions, and this is merely an example in this embodiment. For example, a shooting angle on the right side of the patient is 0°, a shooting angle right above the patient is 90°, a shooting angle on the left side of the patient is 180°, and a shooting angle directly below the patient is 270°, which are merely example descriptions of shooting angles. Or, a few ranges of the shooting angle may be determined or a start point and an end point of the shooting angle may be set as required and based on device limitations. It is understandable that the imaging apparatus may also rotate within a range of 180 degrees, namely, leftward, upward, and rightward, of the patient. The application scenario and the radio therapy device shown in FIG. 2 are merely an example description, and may be adaptively changed based on different use demands. For example, the patient fixing structure may also be a bracket configured to fix a patient in an upright posture.

In a specific application scenario of an image-guided method provided in FIG. 2, including but not limited to a treatment couch 10, an imaging apparatus 20, and a patient 30, the imaging apparatus 20 can rotate 360° around the patient, and can image the target object at any angle. In an example, when the radio therapy device includes an imaging apparatus, the imaging apparatus images the target object at a few shooting angles respectively. For example, the imaging apparatus rotates 360° around the patient to obtain an image of the target object. When the shooting angles are 0° and 90°, or when the shooting angles are 30° and 120°, an angle between the two shooting angles is 90°. In another example, when the radio therapy device includes two imaging apparatuses, an angle between the two imaging apparatuses may be set as 90°. The two imaging apparatuses can rotate 360° around the treatment couch. Therefore, either of the two imaging apparatuses can image the target object at a few shooting angles respectively. For example, the two imaging apparatuses both rotate 360° around the patient to obtain an image of the target object. When a shooting angle of the first imaging apparatus is 50°, a shooting angle of the second imaging apparatus is 140°. It is understandable that the angle between the two imaging apparatuses may be set based on actual situations. This is not limited in the present disclosure. It is understandable that the two imaging apparatuses may also be fixedly arranged around the treatment couch. The angle between the two imaging apparatuses may be 90° or other angles. The angle between the two imaging apparatuses may be set based on the actual situations. This is not limited in the present disclosure.

The planned image refers to an image of the target object acquired in the planning stage, such as: a computed tomography (CT) image, an MRI image, or a PET image. The planning stage means that before radio therapy is performed on the patient, it is necessary to image the target area of the patient, and formulate a treatment plan for the patient based on a target area image of the affected part. In the planning stage, when imaging a target area of the patient, a therapist will first fix a position of the patient on a diagnostic couch by, if the target area of the patient is in his head, fixing a position of the head of the patient with a stereotaxic head frame or mask, while, if the target area of the patient is in his body, fixing a position of the body of the patient with a negative pressure bag; and then imaging the patient after completing the position fixing. Here, a CT image before radio therapy is taken as an example. The CT image is obtained as follows: obtaining a plurality of two-dimensional cross-sectional images through profile scanning around a site of a human body using X-rays together with a detector one by one, and reconstructing the plurality of two-dimensional cross-sectional images by a system into a three-dimensional image, which is used as the CT image. The CT image in the present disclosure may be a three-dimensional image obtained by imaging the target object using a CT imaging technology. The controller of the radio therapy device may acquire the CT image from a CT imaging device through communication connection, or from a related memory or other systems through communication connection. The CT imaging technology may be a cone beam CT (CBCT) technology, a single slice helical CT (SSCT) technology, a multi-slice helical CT (MSCT) technology, or the like. The CT image is obtained before radiotherapy of the patient, and can denote an initial position of the affected part of the patient. The treatment plan is formulated based on the CT image. The treatment plan may include: the number of target sites, shapes of the target sites, a treatment duration of each target site, a planned dose of each target site, and the like. The planned image in embodiments of the present disclosure is not limited to a CT image, but may also be an MRI image or a PET image. This is not limited in the embodiments of the present disclosure.

The rotation offset is generated by a position difference of the target object in the planning stage and the treatment stage. It should be noted that the planning stage means that it is necessary to image the target object before radio therapy is performed on the patient, and formulate the treatment plan for the patient based on the planned image of the target object. After completing the treatment plan, the patient enters the treatment stage. The treatment stage is divided into two stages. The first stage is a positioning stage. In the positioning stage, the patient needs to be positioned, such that the target object overlaps with an isocenter of a treatment device. The second stage is a real-time image-guided treatment stage. Both the positioning stage and the real-time image-guided treatment stage belong to the treatment stage. The positioning stage is before the real-time image-guided treatment stage. Here, in order to describe a sequential relationship in the treatment process, the positioning stage is additionally provided between the planning stage and the real-time image-guided stage. There may be a situation in the positioning stage, for example, the target area of the patient is aligned with the isocenter, e.g., the head, but the head of the patient rotates with the isocenter as a rotation point, for example: the head deflects upward or downward or leftward or rightward, and a three-dimensional treatment couch is used as the treatment couch during positioning, thus failing to compensate for the above rotation offset in the positioning stage, such that the head position of the patient rotates in the positioning stage relative to the position in the planning stage. Therefore, the target area image of the patient under treatment is a distorted image relative to the target area image of the patient in the planning stage. If the two images are registered, the registration accuracy will be greatly reduced. Therefore, it is necessary to acquire the rotation offset of the target object in the treatment stage, where the rotation offset may be determined in the positioning stage, or may be determined in the real-time image-guided stage. This is not limited in the present disclosure. If the rotation offset is determined in the real-time image-guided stage, then it is not necessary to determine the rotation offset in the positioning stage.

The real-time image refers to an image obtained by real-time imaging of the target object by the imaging apparatus in the real-time image-guided stage of the treatment process.

Step 102: determining a tracking offset based on the rotation offset, the planned image, and the real-time image.

The tracking offset is used for tracking the target object.

During radio therapy, the target area of the patient is tracked based on the rotation offset obtained in the positioning stage or the real-time image-guided treatment stage in combination with the planned image and the real-time image. A key technology of radio therapy is to maintain precise positioning of the target area of the patient during radio therapy. Therefore, during radio therapy, it is generally necessary to track the target area of the patient to realize precise positioning, and guide the treatment of the patient based on the tracking offset, thereby reducing the radio therapy error caused by position change of the target area due to positioning. In the present disclosure, a tracking offset is determined based on a rotation offset, a planned image, and a real-time image, a target object is tracked based on the tracking offset, and the processes described in the above steps 101 and 102 are constantly repeated with imaging using an imaging apparatus in a treatment stage of a patient, thus realizing the tracking the target object. The tracking of the target object based on the tracking offset can compensate for the treatment error caused by target area deflection. The treatment error may be caused by an angle between the target object and a horizontal plane due to posture deflection of the patient, or be caused by an angle between the target object and a vertical plane due to patient rotation in the horizontal plane. This is not limited in the present disclosure. In the present disclosure, the target object is tracked based on the tracking offset, thereby improving the registration accuracy of the target area with the planed image before treatment of the patient, and improving the treatment accuracy of the patient.

Embodiment II

Figure 3:
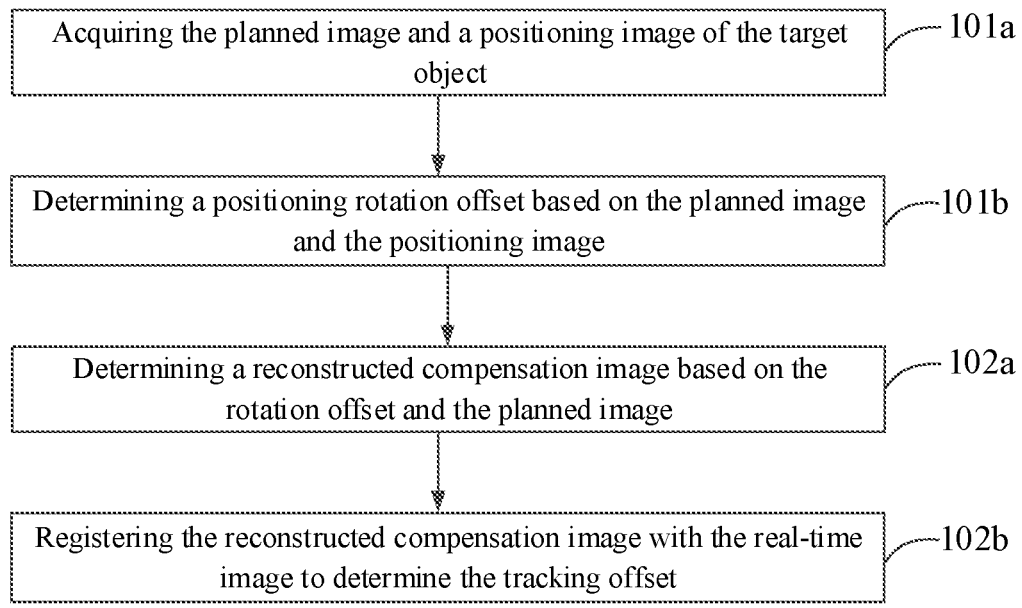
FIG. 3 is a schematic flowchart of another image-guided method provided in an embodiment of the present disclosure.

Based on steps 101 and 102 described in the above Embodiment I, Embodiment II provides another image-guided method to describe a specific implementation of step 101 and step 102 in detail. As shown in FIG. 3, FIG. 3 is a schematic flowchart of another image-guided method in an embodiment of the present disclosure. A rotation offset is obtained in a treatment stage, and the treatment stage includes a positioning stage and a real-time image-guided stage, where the rotation offset may be acquired in the positioning stage, or may be acquired in the real-time image-guided stage. In FIG. 3, acquiring the rotation offset in the positioning stage is taken as an example for description. The rotation offset is a positioning rotation offset, and the positioning rotation offset is a rotation offset of the target object determined in the positioning stage. Step 101*a* and step 101*b* in FIG. 3 are specific implementations of step 101 in Embodiment I. Steps 101*a* and 101*b* are processes of determining the positioning rotation offset in the positioning stage.

Step 101*a*: acquiring the planned image and a positioning image of the target object.

The planned image of the target object is acquired in the planning stage, and the treatment plan for the patient is formulated based on the planned image of the target object. After completing the treatment plan, the patient enters the positioning stage of the treatment process, and a posture and a position of the patient are changed under the guidance of laser rays emitted from the radio therapy device, such that the laser rays are aligned with the target object, and the target object overlaps with a virtual isocenter of the radio therapy device. Then, the patient is moved based on a known distance between the virtual isocenter and the isocenter, such that the target object overlaps with the isocenter of the radio therapy device to achieve positioning of the target object. For example, based on the planned image of the patient, the therapist will draw a cross mark for denoting a position of the target object on the body surface of the patient, and then position the patient using a laser lamp. The laser lamp can determine a point in space, which is known as the virtual isocenter. The target object overlaps with the virtual isocenter by moving the treatment couch, and then the target object overlaps with the isocenter of the radio therapy device by moving the treatment couch based on the known distance between the virtual isocenter and the isocenter of the radio therapy device. In the positioning stage of the treatment process, an image of the target object is acquired as the positioning image.

The planned image is obtained by imaging the target object in the planning stage. The planned image obtained in the planning stage is an undistorted image. Because of position deflection of the patient, the positioning image of the target object is a distorted image in the positioning stage of the treatment process. Therefore, it is necessary to determine the rotation offset based on the planned image and the positioning image.

Step 101*b*: determining a positioning rotation offset based on the planned image and the positioning image.

It should be noted that the rotation offset in Embodiment II of the present disclosure is described using the positioning rotation offset obtained in the positioning stage as an example, and the positioning rotation offset is also the rotation offset.

When positioning the patient, body posture of the patient tends to rotate, such that the target object deflects. The positioning accuracy will affect the treatment accuracy of the patient. In the embodiment of the present disclosure, the positioning image of the target object is acquired in the positioning stage of the treatment process, the positioning image in the positioning stage is used for positioning validation, and a positioning offset is determined based on the positioning image and the planned image, where the positioning offset includes a translation offset and a rotation offset, and positioning adjustment or validation is performed on the patient before treatment based on the translation offset, such that the target area of the patient overlaps with the isocenter.

For example, in the embodiment of the present disclosure, the patient is positioned using the laser lamp relying on a mark on the body surface of the patient in step 101*a*, the accuracy of which is limited. In an implementable way, after positioning the patient using the laser lamp, a position of the treatment couch may be adjusted based on the translation offset determined in step 101*b*, such that the target area of the patient overlaps with the isocenter; and in another implementable way, the target object may be positioned directly based on the translation offset determined in step 101*b*. Specifically, the fixing structure of the patient can be controlled to move based on the translation offset, such that the target object overlaps with the isocenter of the radio therapy device, thus further improving the positioning accuracy of the patient.

It should be noted that when determining the rotation offset, it is necessary to perform image registration on the planned image and the positioning image. The image registration is a process of matching and superimposing two or more images acquired at different time or by different sensors (e.g., imaging devices) or under different conditions (e.g., climate, illuminance, camera position, and angle), and means to seek one (or a series of) spatial transformation(s) for one image, such that a point on the transformed image is spatially consistent with a corresponding point on another image. For a medical image providing anatomical shape information of an organ, such consistency may mean that a same anatomical point on a human body has a same spatial position on two matched images, i.e., the position is consistent and the angle is consistent. During image registration, two to-be-registered images should have a same dimension, i.e., both are two-dimensional images or both are three-dimensional images. In a registration mode, the two to-be-registered images are both two-dimensional images, and are planarly registered; while in another registration mode, the two to-be-registered images are both three-dimensional images, and are spatially registered. In step 101*b*, the determining the rotation offset may be implemented by two-dimensional registration or three-dimensional registration. Here, two specific examples are provided for description. In the two examples, the target object may be the target area of the patient, e.g., an intracranial tumor.

In the first example, three-dimensional image registration is taken as an example: N positioning images are reconstructed to obtain a three-dimensional image, the N positioning images are obtained by imaging the target object at N different shooting angles respectively, the N is a natural number greater than 2; and the three-dimensional image is registered with the planned image to obtain the positioning rotation offset.

When the radio therapy device includes an imaging apparatus, the imaging apparatus rotates 360 degrees around the fixing structure that fixes the patient's body with a longitudinal direction of the patient's body as an axis. At the same time, the imaging apparatus emits an imaging beam at a certain frequency to image the target object to obtain positioning images at N different shooting angles, and reconstructs a three-dimensional image of the target object using the N positioning images. It is understandable that the N shooting angles may be uniformly distributed. For example, when N is equal to 6, the 6 shooting angles may be 0°, 60°, 120°, 180°, 240°, and 300°. Then, the reconstructed three-dimensional image of the target object is registered with the planned image to obtain a positioning offset between the three-dimensional image of the target object and the planned image. The positioning offset includes a translation offset and a rotation offset. When the radio therapy device includes an imaging apparatus, the radio therapy device helps to reduce the complexity and costs of the radio therapy device.

When the radio therapy device includes two imaging apparatuses, in an application scenario, either of the two imaging apparatuses may rotate 360 degrees or less than 360 degrees around the fixing structure that fixes the patient's body to image the target object, and superimpose target area images formed by the two imaging apparatuses for use as a final positioning image, thus further improving the imaging accuracy of the target object; while in another application scenario, the first imaging apparatus rotates 180 degrees around the fixing structure that fixes the patient's body, and the second imaging apparatus rotates 180 degrees around the fixing structure that fixes the patient's body in a direction opposite to a rotation direction of the first imaging apparatus. After imaging the target object, the two imaging apparatuses can obtain N positioning images at different shooting angles, reconstruct the N positioning images into the three-dimensional image of the target object, and then register the reconstructed three-dimensional image of the target object with the planned image to obtain a positioning offset between the positioning image and the planned image. The positioning offset includes a translation offset and a rotation offset. When the radio therapy device includes two imaging apparatuses, a rotation angle of the imaging apparatus can be reduced, and a duration for imaging the target object can be reduced, thereby further improving the imaging efficiency of the target object.

In the second example, two-dimensional image registration is taken as an example: the planned image is reconstructed at two orthogonal shooting angles respectively to obtain two reconstructed images corresponding to the two orthogonal shooting angles; two positioning images are registered with the two reconstructed images to obtain two second offsets, the two positioning images are obtained by imaging the target object at the two orthogonal shooting angles respectively; and a positioning rotation offset is obtained based on the two second offsets.

It should be noted that the two orthogonal shooting angles refer to two shooting angles with an angle of 90° therebetween. For example, one shooting angle is 8°, the other shooting angle is 98°, and then the two shooting angles are referred to as two orthogonal shooting angles.

When the registration mode is two-dimensional registration, one of the to-be-registered images is the planned image. Here, the planned image is, e.g., a CT image. The planned image is a three-dimensional image. The two positioning images are two-dimensional images obtained by the imaging apparatus at two different shooting angles. Therefore, it is necessary to reduce dimensionality of the three-dimensional image to obtain a two-dimensional image, and then reconstruct the planned image into a digitally reconstructed radiograph (DRR for short) image at two orthogonal shooting angles by two-dimensional registration. In the present disclosure, a reconstructed image is used to denote the DRR image, and the two orthogonal shooting angles are identical to two orthogonal shooting angles when acquiring the two positioning images. For example, digitally reconstructed radiograph is a two-dimensional image generated from a three-dimensional CT image through a mathematical simulation algorithm. The digitally reconstructed radiograph may be applied to the fields, such as CT image simulation and positioning, image-guided radiotherapy (IGRT), and computer-aided surgery. The planned image is reconstructed at two orthogonal shooting angles. For example, the planned image is reconstructed in a direction where the shooting angle is 0° to obtain a reconstructed image at an angle of 0°, and is reconstructed in a direction where the shooting angle is 90° to obtain a reconstructed image at an angle of 90°. When an angle between two shooting angles is 90°, the registration accuracy of images can be improved.

When the radio therapy device includes an imaging apparatus, the imaging apparatus images the target object, e.g., at angles of 0° and 90° respectively, to obtain two two-dimensional images of the target object, i.e., two positioning images; reconstruct the planned image at the angles of 0° and 90°, to obtain two reconstructed images, register the two positioning images with the two reconstructed images to obtain two two-dimensional offsets; and compute the positioning offset of the target object based on the two two-dimensional offsets, the positioning offset including the rotation offset and the translation offset. When the radio therapy device includes an imaging apparatus, the radio therapy device helps to reduce the complexity and costs of the radio therapy device.

It is understandable that the imaging apparatus may also image the target object at 10° and 100°, and reconstruct the planned image at the angles of 10° and 100°; or the imaging apparatus may also image the target object at 90° and 180°, and reconstruct the planned image at the angles of 90° and 180°, as long as an angle between the two imaging angles is 90°. This is not limited in the present disclosure. In addition, it should be noted that the imaging apparatus may also image the target object at any other two angles respectively. The embodiment of the present disclosure shows the imaging the target object at two angles with an angle of 90° therebetween. When the angle between the two angles is 90°, the registration accuracy can be improved when the two positioning images are registered with the two reconstructed images.

When the radio therapy device includes two imaging apparatuses, one of the two imaging apparatuses is at a position at a shooting angle of 0°, the other one of the two imaging apparatuses is at a position at a shooting angle of 90°, and an angle between the two imaging apparatuses is 90°. The two imaging apparatuses both image the target object to obtain two two-dimensional images of the target object at the two angles, i.e., two positioning images, where the angle between the two angles is 90°; reconstruct the planned image at the angles of 0° and 90°, to obtain two reconstructed images; register the two positioning images with the two reconstructed images to obtain two two-dimensional offsets of the target object; and compute the positioning offset of the target object based on the two two-dimensional offsets, the positioning offset including the rotation offset and the translation offset. When the radio therapy device includes two imaging apparatuses, a rotation angle of the imaging apparatus can be reduced, and a duration for imaging the target object can be reduced, thereby further improving the imaging efficiency of the target area.

It is understandable that an imaging apparatus is at a position at a shooting angle of 70°, another imaging apparatus is at a position at a shooting angle of 160°, and an angle between the two imaging apparatuses is also 90°. The two imaging apparatuses both image the target object to obtain two two-dimensional images of target object at two angles, reconstruct the planned image at the angles of 70° and 160°, to obtain two reconstructed images; and register the two positioning images with the two reconstructed images to obtain two two-dimensional offsets of the target object; and compute the positioning offset of the target object based on the two two-dimensional offsets, the positioning offset including the translation offset and the rotation offset. It should be noted that the angle between the two imaging apparatuses may also be other degrees. The embodiment of the present disclosure only shows two imaging apparatuses with an angle of 90°, but do not mean that the present disclosure is limited to this. When the angle between the two imaging apparatuses is 90°, the registration accuracy can be improved when the two positioning images are registered with the two reconstructed images.

In the embodiment of the present disclosure, a planned image of a target object is acquired before a treatment process, then a positioning image of the target object is acquired in a positioning stage of the treatment process, and two-dimensional or three-dimensional registration is performed on the positioning image and the planned image, a translation offset and a rotation offset are determined, and positioning adjustment or positioning validation is performed on a patient based on the translation offset, to further improve the positioning accuracy of the patient; or, a fixing structure of the patient may be controlled to move based on the translation offset, to correct a relative position deviation between a current position state of the target object and an initial position state of the target object, such that the target object overlaps with an isocenter of a radio therapy device. Here, the target object is used for indicating a target area of the patient, e.g., an intracranial tumor.

After the target object overlaps with the isocenter of the radio therapy device based on the translation offset, a real-time image of the target object is acquired. The real-time image of the target object is a two-dimensional image. Two real-time images are used in the embodiment of the present disclosure. When the radio therapy device includes two imaging apparatuses, the two imaging apparatuses image the target object simultaneously at two different shooting angles to obtain real-time images corresponding to the two angles. The real-time images are two-dimensional images. The angle between the two imaging apparatuses may be 45° to 135°. In the embodiment of the present disclosure, 90° is taken as an example for description, but does not mean that the present disclosure is limited to this. When the radio therapy device includes an imaging apparatus, the imaging apparatus images the target object at two different angles respectively, to obtain two real-time images. The real-time image is a two-dimensional image. An angle between the two different angles may be 45° to 135°. In the embodiment of the present disclosure, two angles with an angle of 90° there between are taken as an example for description, but do not mean that the present disclosure is limited to these.

Step 102: determining a tracking offset based on the rotation offset, the planned image, and the real-time image in Embodiment I may also be executed based on the acquired real-time image. Step 101a and step 101b are determining the rotation offset in the positioning stage. Of course, the rotation offset may also be determined in the real-time image-guided stage. This is not limited in the present disclosure. If the rotation offset is determined in the real-time image-guided stage, then it is not necessary to determine the rotation offset in the positioning stage. Alternatively, as shown in FIG. 3, FIG. 3 is a schematic flowchart of another image-guided method in an embodiment of the present disclosure. The rotation offset in FIG. 3 is determined in the positioning stage, and is only taken as an example for description. It is understandable that the rotation offset may also be determined in the real-time image-guided stage. Step 102a and step 102b in FIG. 3 are specific implementations of step 102 in Embodiment I. Steps 102a and 102b are processes of determining the tracking offset.

Step 102a: determining a reconstructed compensation image based on the rotation offset and the planned image.

Step 102b: registering the reconstructed compensation image with the real-time image to determine the tracking offset.

Step 102a and step 102b may have the following specific implementations. Here, two examples are provided for description.

In the first example, the planned image is compensated for based on the rotation offset to obtain a compensated planned image; and the compensated planned image is reconstructed at a first angle and a second angle respectively, to obtain two reconstructed compensation images corresponding to the first angle and the second angle. The two reconstructed compensation images are registered with the two real-time images respectively to obtain two first offsets, where the two real-time images are obtained by imaging the target object at the first angle and the second angle respectively; and the tracking offset is computed based on the two first offsets.

It should be noted that the first angle and the second angle refer to two different shooting angles.

Figure 4:
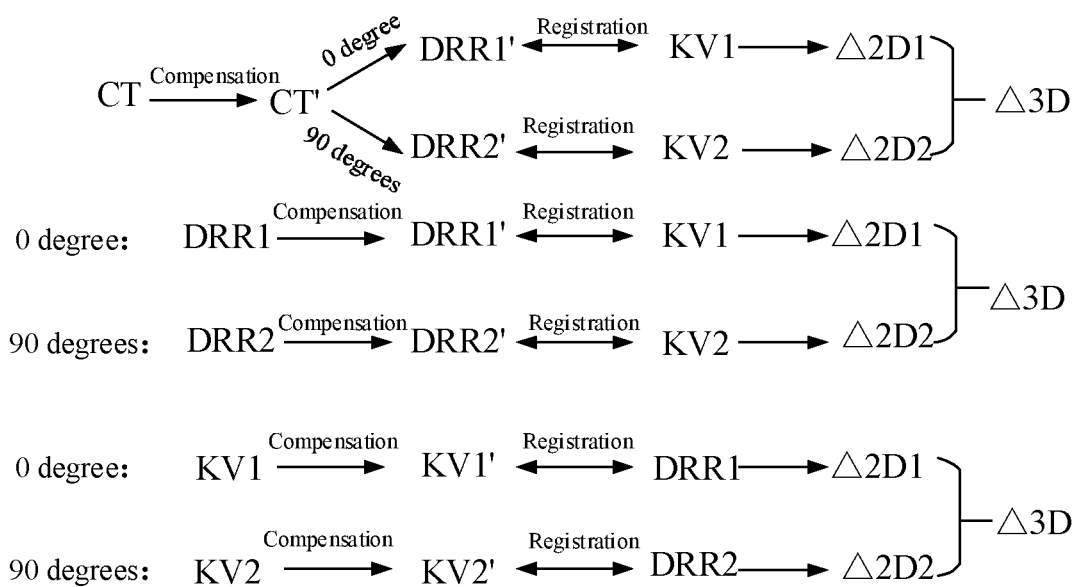
FIG. 4 is a schematic diagram of a method for computing an offset provided in an embodiment of the present disclosure.

Specifically, as shown in FIG. 4, FIG. 4 is a schematic diagram of a method for computing an offset provided in an embodiment of the present disclosure. A rotation offset of a planned image is compensated for based on a rotation offset obtained in a positioning stage or a real-time image-guided stage, to obtain a compensated planned image. In FIG. 4, the planned image being a CT image is taken as an example for example description. The planned image may also be an MRI image, a PET image, or the like. This is not limited in the embodiment of the present disclosure. In FIG. 4, CT denotes the planned image. Alternatively, the planned image may be rotated based on the rotation offset to obtain the compensated planned image. In FIG. 4, CT' denotes the compensated planned image; and the compensated planned image is reconstructed at a first angle and a second angle, to obtain two reconstructed compensation images. In FIG. 4, DRR' denotes a reconstructed compensation image, and two real-time images of a target area of a patient are obtained at the first angle and the second angle. In FIG. 4, the target area of the patient is imaged at shooting angles of 0° and 90°, and the compensated planned image is reconstructed at the shooting angles of 0° and 90° to obtain reconstructed compensation images. In the embodiment of the present disclosure, the two different angles of 0° and 90° are used as example descriptions, but do not mean that the present disclosure is limited to these. In FIG. 4, DRR1' denotes a reconstructed compensation image at a shooting angle of 0°, and DRR2' denotes a reconstructed compensation image at a shooting angle of 90°. KV1 denotes a real-time image of the target area of the patient at a shooting angle of 0°, and KV2 denotes a real-time image of the target area of the patient at a shooting angle of 90°. The two reconstructed compensation images are registered with the two real-time images of the target area of the patient to obtain two two-dimensional offsets of the target area of the patient. $\Delta 2D1$ denotes a two-dimensional offset at a shooting angle of 0°, and $\Delta 2D2$ denotes a two-dimensional offset at a shooting angle of 90°. A tracking offset of the target area of the patient is computed based on the two two-dimensional offsets. The tracking offset is a three-dimensional offset. In FIG. 4, Δ3D denotes the tracking offset.

In the second example, the planned image is reconstructed at the first angle and the second angle respectively, to obtain two reconstructed images corresponding to the first angle and the second angle; and the two reconstructed images are compensated for respectively based on the rotation offset, to obtain two reconstructed compensation images. The two reconstructed compensation images are registered with the two real-time images respectively to obtain two first offsets, where the two real-time images are obtained by imaging the target object at the first angle and the second angle respectively; and the tracking offset is computed based on the two first offsets.

Specifically, as shown in FIG. 4, FIG. 4 is a schematic diagram of a method for computing an offset provided in an embodiment of the present disclosure. In FIG. 4, the planned image being a CT image is taken as an example for example description. The planned image may also be an MRI image, a PET image, or the like. This is not limited in the embodiment of the present disclosure. In FIG. 4, CT denotes the planned image. The planned image is reconstructed at the first angle and the second angle, to obtain two reconstructed images, and two real-time images of the target area of the patient are obtained at the first angle and the second angle. In FIG. 4, the target area of the patient is imaged at the shooting angles of 0° and 90°, and the planned image is reconstructed at the shooting angles of 0° and 90° to obtain reconstructed images. In the embodiment of the present disclosure, the two different angles of 0° and 90° are used as example description, but do not mean that the present disclosure is limited to these. In FIG. 4, DRR1 denotes a reconstructed image at a shooting angle of 0°, and DRR2 denotes a reconstructed image at a shooting angle of 90°. The two reconstructed images are compensated for respectively based on the rotation offset acquired in the positioning stage or the real-time image-guided stage. Alternatively, the two reconstructed images are rotated based on the rotation offset to obtain two reconstructed compensation images. The two reconstructed compensation images are registered with the corresponding two real-time images of the target area of the patient to obtain two two-dimensional offsets of the target area of the patient. The tracking offset of the target area of the patient is computed based on the two two-dimensional offsets. The tracking offset is a three-dimensional offset, and the target area of the patient can be tracked based on the tracking offset.

Alternatively, step 102 may also have the following specific implementations. The two real-time images are compensated for based on the rotation offset to obtain two real-time compensation images, and the two real-time images are obtained by imaging the target object at a third angle and a fourth angle respectively; the planned image is reconstructed at the third angle and the fourth angle respectively, to obtain two reconstructed images corresponding to the third angle and the fourth angle; and the two real-time compensation images are registered with the two reconstructed images to determine the tracking offset.

It should be noted that the third angle and the fourth angle refer to two different shooting angles. Values of the first angle, the second angle, the third angle and the fourth angle do not affect each other, as long as the first angle is different from the second angle, and the third angle is different from the fourth angle.

Specifically, as shown in FIG. 4, FIG. 4 is a schematic diagram of a method for computing an offset provided in an embodiment of the present disclosure. The two real-time images of the target area of the patient are compensated for based on the rotation offset obtained in the positioning stage or the real-time image-guided stage. Alternatively, the real-time images of the target area of the patient are rotated based on the rotation offset to obtain real-time compensation images of the target area of the patient. In FIG. 4, KV' denotes a KV compensation image, KV1' denotes a real-time compensation image at a shooting angle of 0°, and KV2' denotes a real-time compensation image at a shooting angle of 90°. In the embodiment of the present disclosure, the two different angles of 0° and 90° are used as example description, but do not mean that the present disclosure is limited to these. The planned image is reconstructed at the third angle and the fourth angle, to obtain two reconstructed images, and acquire two real-time images at the third angle and the fourth angle. In FIG. 4, the planned image is reconstructed at the shooting angles of 0° and 90° to obtain reconstructed images; the two reconstructed images are registered with the two real-time compensation images to obtain two two-dimensional offsets of the target area of the patient; and the tracking offset of the target area of the patient is computed based on the two two-dimensional offsets. The tracking offset is a three-dimensional offset, and the target area of the patient can be tracked based on the tracking offset. For example, in an implementable way, the target area of the patient can be tracked based on the tracking offset, such that an initial position state of the target area of the patient and a current position state of the target area of the patient in the treatment process correspond to each other, thereby correcting a relative position deviation between the current position state of the target area of the patient and the initial position state of the target area of the patient, and, e.g., controlling at least one of a moving position of a therapeutic radioactive ray emitting structure and a moving position of a patient fixing structure by a controller, such that an irradiation position (radiation field position) of the therapeutic radioactive ray emitting structure matches the current position state of the target object. In addition, the controller can further instruct an operator to move the treatment couch or multileaf grating blades by outputting a registration result in real time to correct the patient's position or the radiation field position. The multileaf grating blades may be configured to control a direction of rays. In another possible implementation, a preset threshold may also be set to compare with the relative position deviation. When the relative position deviation is less than or equal to the preset threshold, the treatment can be continued without performing any operation. It should be understood that the preset threshold may be determined based on an actual application scenario and application requirements. The initial position state of the target area of the patient refers to a position state of the planned image obtained in the planning stage. Image guidance on the target object may be implemented by, e.g., moving the treatment couch based on the initial position state and the current position state, to compensate for image distortion caused by target area deflection. The image distortion may be caused by an angle between the target object and a horizontal plane due to posture deflection of the patient, or be caused by an angle between the target object and a vertical plane due to patient rotation in the horizontal plane. This is not limited in the present disclosure. In the present disclosure, the target object is tracked based on the tracking offset, thereby improving the registration accuracy of the target area with the planed image before treatment of the patient, and improving the treatment accuracy of the patient.

In the above embodiments, the tracking offset is a three-dimensional offset determined at two different shooting angles based on the rotation offset, the real-time image, and the planned image, i.e., first computing two two-dimensional offsets, and then computing the three-dimensional offset of the target object based on the two two-dimensional offsets. It is understandable that the tracking offset may also be determined by computing at least three two-dimensional offsets at least three shooting angles, and then computing the three-dimensional offset of the target object based on the at least three two-dimensional offsets. For example, in an application scenario, the three-dimensional offset may be computed comprehensively based on two-dimensional offsets at shooting angles of 10°, 100°, 190°, and 280°, the relative position deviation between the current position state of the patient and the initial position state of the patient may be corrected based on the three-dimensional offset, and the tracking offset may be computed based on the at least three two-dimensional offsets, thereby improving the computation accuracy of the tracking offset, and improving the treatment accuracy of the patient by real-time image guidance based on the tracking offset.

After a target object overlaps with an isocenter of a radio therapy device, a real-time image of the target object is acquired, a tracking offset is determined based on a rotation offset, a planned image, and the real-time image, and finally an irradiation position (radiation field position) of therapeutic radioactive rays is adjusted to match a current position state of the target object based on the tracking offset, to realize image guidance on the target object. Further, with the rotation of an imaging apparatus, processes described in the following steps are constantly repeated: acquiring the real-time image of the target object, and determining the tracking offset based on the rotation offset, the planned image, and the real-time image, thereby realizing the tracking the target object.

In the present disclosure, before image registration, the rotation offset of the obtained reconstructed image or the real-time image of the target object is compensated for, such that a real-time image of a target area of a patient and a reconstructed image of the planned image are in a same patient posture state, and the registration accuracy is higher when a compensated real-time image is registered with the reconstructed image, or a compensated reconstructed image is registered with the real-time image, thereby further improving the treatment accuracy of the patient.

Embodiment III

Figure 5:
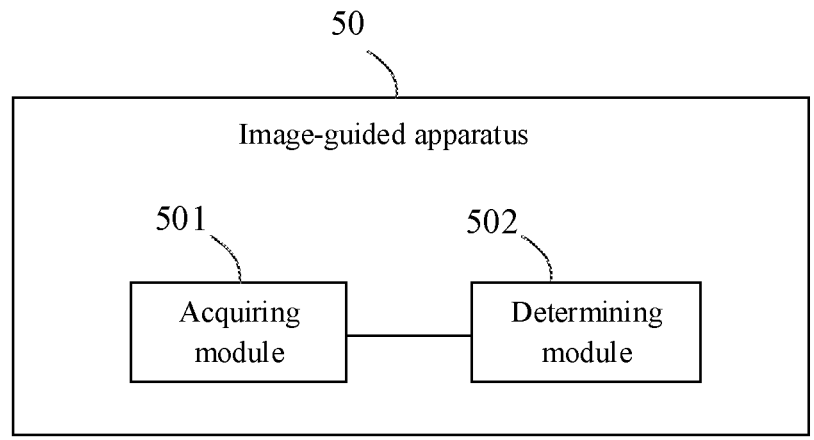
FIG. 5 is a schematic structural diagram of an image-guided apparatus provided in an embodiment of the present disclosure.

The embodiment of the present disclosure provides an image-guided apparatus, which is applied to a medical device. The radio therapy device may include, but is not limited to, a patient fixing structure and an imaging apparatus. The radio therapy device can control the movement of the fixing structure, such that a patient moves along with the patient fixing structure, the imaging apparatus can rotate around the patient fixing structure, and a medical image of the patient on the patient fixing structure can be taken at a few shooting angles. In an implementable scenario, an image-guided method may be installed on a radio therapy device (e.g., the imaging apparatus or an operating table) in the form of software, thus achieving an image-guided process in a medical activity. As shown in FIG. 5, FIG. 5 is a schematic diagram of an image-guided apparatus provided in an embodiment of the present disclosure. The image-guided apparatus 50 includes: an acquiring module 501, and a determining module 502.

The acquiring module 501 is configured to acquire a rotation offset, a planned image, and a real-time image of a target object, the rotation offset being generated by a position difference of the target object in a planning stage and a treatment stage; and the determining module 502 is configured to determine a tracking offset based on the rotation offset, the planned image, and the real-time image, the tracking offset being used for tracking the target object.

Alternatively, the rotation offset is a positioning rotation offset, and the positioning rotation offset is a rotation offset of the target object determined in a positioning stage.

Alternatively, the acquiring module 501 is further configured to acquire the planned image and a positioning image of the target object; and determine the positioning rotation offset based on the planned image and the positioning image.

Alternatively, the determining module 502 further includes a first determining unit and a second determining unit. The first determining unit is configured to determine a reconstructed compensation image based on the rotation offset and the planned image; and the second determining unit is configured to register the reconstructed compensated image with the real-time image to determine the tracking offset.

Alternatively, the first determining unit is further configured to compensate for the planned image based on the rotation offset to obtain a compensated planned image; and reconstruct the compensated planned image at a first angle and a second angle respectively, to obtain two reconstructed compensation images corresponding to the first angle and the second angle.

Alternatively, the first determining unit is further configured to reconstruct the planned image at the first angle and the second angle respectively, to obtain two reconstructed images corresponding to the first angle and the second angle; and compensate for the two reconstructed images respectively based on the rotation offset, to obtain two reconstructed compensation images.

Alternatively, the second determining unit is configured to register the two reconstructed compensation images with the two real-time images respectively to obtain two first offsets, where the two real-time images are obtained by imaging the target object at the first angle and the second angle respectively; and compute the tracking offset based on the two first offsets.

Alternatively, the determining module 502 is further configured to compensate for the two real-time images based on the rotation offset to obtain two real-time compensation images, the two real-time images being obtained by imaging the target object at a third angle and a fourth angle respectively; reconstruct the planned image at the third angle and the fourth angle respectively, to obtain two reconstructed images corresponding to the third angle and the fourth angle; and register the two real-time compensation images with the two reconstructed images to determine the tracking offset.

Alternatively, the acquiring module 501 is further configured to reconstruct N positioning images to obtain a three-dimensional image, the N positioning images being obtained by imaging the target object at N different shooting angles respectively, the N being a natural number greater than 2; and register the three-dimensional image with the planned image to obtain the positioning rotation offset.

Alternatively, the acquiring module 501 is further configured to reconstruct the planned image at two orthogonal angles respectively to obtain two reconstructed images corresponding to the two orthogonal angles; register two positioning images with the two reconstructed images to obtain two second offsets, the two positioning images being obtained by imaging the target object at the two orthogonal angles respectively; and obtain a positioning rotation offset based on the two second offsets.

It is understandable that, according to an alternative implementation of the above image-guided method, the image-guided apparatus 50 can implement any one of the above image-guided methods with the help of corresponding structures and configurations, specific details of which will not be repeated.

In the embodiment corresponding to FIG. 5, the image-guided apparatus 50 is presented in the form of a functional unit/functional module. The "unit/module" here may refer to an application specific integrated circuit (ASIC), a processor executing one or more software or firmware programs, a memory, an integrated logic circuit, and/or other components that can provide the above functions. For example, at least a part of functions of at least one of the units and modules may be implemented by the processor through executing program code stored in the memory.

Embodiment IV

Figure 6:
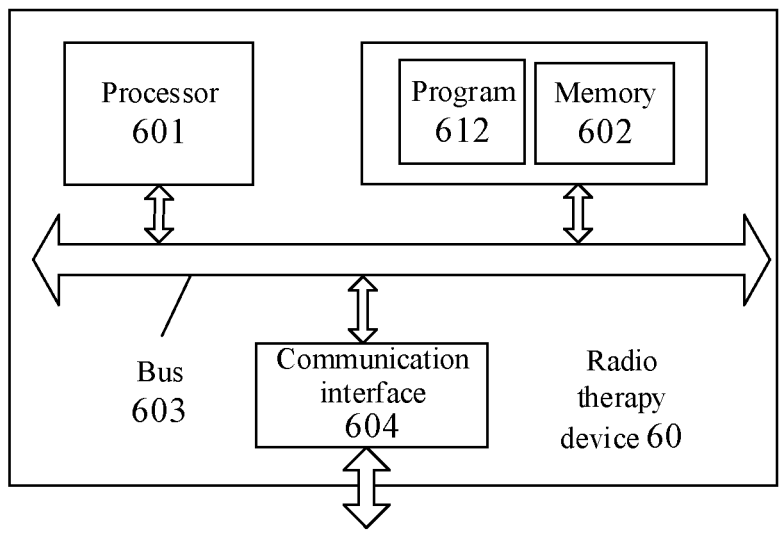
FIG. 6 is a structural diagram of a radio therapy device provided in an embodiment of the present disclosure.

Based on the image-guided method described in the above Embodiment I or Embodiment II, an embodiment of the present disclosure provides a radio therapy device. As shown in FIG. 6, FIG. 6 is a structural diagram of a radio therapy device provided by an embodiment of the present disclosure. The radio therapy device 60 includes: at least one processor 601; a memory 602 storing at least one program 612, a bus 603, and a communication interface 606. The at least one processor 601, the memory 602, and the communication interface 606 communicate with each other through the bus 603, and the at least one program, when executed by the at least one processor 601, causes the at least one processor 601 to implement the image-guided method described in Embodiment I or Embodiment II.

Specifically, the processor 601 is configured to acquire a rotation offset, a planned image, and a real-time image of a target object, the rotation offset being generated by a position difference of the target object in a planning stage and a treatment stage; and
   determine a tracking offset based on the rotation offset, the planned image, and the real-time image, the tracking offset being used for tracking the target object.

Alternatively, the rotation offset is a positioning rotation offset, and the positioning rotation offset is a rotation offset of the target object determined in a positioning stage.

Alternatively, the processor 601 is further configured to acquire the planned image and a positioning image of the target object; and determine the positioning rotation offset based on the planned image and the positioning image.

Alternatively, the processor 601 is further configured to determine a reconstructed compensation image based on the rotation offset and the planned image; and register the reconstructed compensated image with the real-time image to determine the tracking offset.

Alternatively, the processor 601 is further configured to compensate for the planned image based on the rotation offset to obtain a compensated planned image; and reconstruct the compensated planned image at a first angle and a second angle respectively, to obtain two reconstructed compensation images corresponding to the first angle and the second angle.

Alternatively, the processor 601 is further configured to reconstruct the planned image at the first angle and the second angle respectively, to obtain two reconstructed images corresponding to the first angle and the second angle; and compensate for the two reconstructed images respectively based on the rotation offset, to obtain two reconstructed compensation images.

Alternatively, the processor 601 is configured to register the two reconstructed compensation images with the two real-time images respectively to obtain two first offsets, where the two real-time images are obtained by imaging the target object at the first angle and the second angle respectively; and compute the tracking offset based on the two first offsets.

Alternatively, the processor 601 is further configured to compensate for the two real-time images based on the rotation offset to obtain two real-time compensation images, the two real-time images being obtained by imaging the target object at a third angle and a fourth angle respectively; reconstruct the planned image at the third angle and the fourth angle respectively, to obtain two reconstructed images corresponding to the third angle and the fourth angle; and register the two real-time compensation images with the two reconstructed images to determine the tracking offset.

Alternatively, the processor 601 is further configured to reconstruct N positioning images to obtain a three-dimensional image, the N positioning images being obtained by imaging the target object at N different shooting angles respectively, the N being a natural number greater than 2; and register the three-dimensional image with the planned image to obtain the positioning rotation offset.

Alternatively, the processor 601 is further configured to reconstruct the planned image at two orthogonal angles respectively to obtain two reconstructed images corresponding to the two orthogonal angles; register two positioning images with the two reconstructed images to obtain two second offsets, the two positioning images being obtained by imaging the target object at the two orthogonal angles respectively; and obtain a positioning rotation offset based on the two second offsets.

The processor 601 may include a central processing unit (CPU, a single-CPU or a multi-CPU), a graphics processing unit (GPU), a microprocessor, an Application-Specific Integrated Circuit (ASIC), a digital signal processor (DSP), a digital signal processing device (DSPD), a programmable logic device (PLD), a field programmable gate array (FPGA), a controller, a microcontroller, or a plurality of integrated circuits configured to control program execution.

The memory 602 may include a read-only memory (ROM) or other types of static storage devices that can store static information and instructions, and a random access memory (RAM) or other types of dynamic storage devices that can store information and instructions, and may also include an electrically erasable programmable read-only memory (EEPROM), a Compact Disc Read-Only Memory (CD-ROM) or other optical disk storage, compact disk storage (including compressed disk, laser disk, compact disk, digital universal disk, Blu-ray disk, or the like), disk storage medium or other magnetic storage devices, or any other medium that can be configured to carry or store desired program codes in the form of instructions or data structures and can be accessed by a computer, but is not limited to the above ones. The memory may be independently provided, or be integrated with the processor.

In a specific implementation, as an embodiment, the processor 601 may include one or more CPUs. In a specific implementation, as an embodiment, the radio therapy device may include a plurality of processors. Each of these processors may be a single-CPU processor or a multi-CPU processor. The processor here may refer to one or more devices, circuits, and/or processing cores for processing data (e.g., computer program instructions).

The radio therapy device may include a general-purpose computer device or a special-purpose computer device. In a specific implementation, the radio therapy device may be, e.g., any one radio therapy device that requires medical image registration, such as a radio therapy device, an image-guided radio therapy device, or an operating table. The computer device may be a desktop computer, a portable computer, a network server, a Personal Digital Assistant (PDA), a mobile phone, a tablet computer, a wireless terminal device, a communication device, an embedded device, or a device with a similar structure.

Embodiment V

Based on the image-guided method described in the above Embodiment I or Embodiment II, an embodiment of the present disclosure provides a computer storage medium storing a computer program. The computer program, when executed by a processor, implements the image-guided method as described in Embodiment I.

The radio therapy device in the embodiment of the present disclosure exists in various forms, including but not limited to:
  (1) a mobile communication device: Such a device is characterized by having mobile communication functions, and is mainly intended to provide voice and data communication. Such a terminal includes: a smart phone (e.g., an iPhone), a multimedia phone, a functional phone, a low-end phone, and the like.
  (2) an ultra-mobile personal computer device: Such a device belongs to a category of personal computers, has computing and processing functions, and generally also has the characteristics of mobile Internet access. Such a terminal includes: a device, such as a PDA, a MID, and a UMPC, e.g., an iPad.
  (3) a portable entertainment device: Such a device can display and play multimedia contents. Such a device includes: an audio player, a video player (e.g., an iPod), a handheld game player, an e-book, a smart toy, and a portable vehicle navigation device.
  (4) a server: A device providing a computing service. The server components include a processor 810, a hard disk, an internal memory, a system bus, etc. A structure of the server is similar to that of a general-purpose computer. But because of the needs for providing a highly reliable service, the requirements in respect of processing capacity, stability, reliability, security, scalability, manageability, etc. are very high.
  (5) other electronic structures having data interaction functions.

So far, specific embodiments of this subject matter have been described. Other embodiments fall within the scope of the appended claims. In some cases, actions disclosed in the appended claims may be performed in different orders and can still achieve desired results. In addition, the processes depicted in the figures are not necessarily required to achieve the desired results in the shown particular order or sequential order. In some embodiments, multitasking and parallel processing may be advantageous.

The system, apparatus, modules or units illustrated in the above embodiments may be specifically implemented by a computer chip or entity, or by a product having a function. A typical implementing device is a computer. Specifically, the computer, e.g., may be a personal computer, a laptop computer, a cellular phone, a camera phone, a smart phone, a personal digital assistant, a medium player, a navigation device, an e-mail device, a game console, a tablet computer, a wearable device, or a combination of any device of these devices.

For ease of description, the above apparatus is described by dividing the apparatus into various units based on functions, and then describing the units respectively. Of course, when the present disclosure is implemented, the functions of the units can be implemented in a same piece or more pieces of software and/or hardware.

Those skilled in the art should understand that the embodiments of the present disclosure may be provided as a method, a system, or a computer program product. Accordingly, the present disclosure may take the form of an entirely hardware embodiment, an entirely software embodiment, or an embodiment combining software and hardware. Further, the present disclosure may take the form of a computer program product embodied on one or more computer-usable storage mediums (including, but not limited to, a disk memory, a CD-ROM, an optical memory, and the like) having computer-usable program code embodied thereon.

The present disclosure is described with reference to the flowcharts and/or block diagrams of the method, device (system), and computer program product according to the embodiments of the present disclosure. It should be understood that each process and/or block in the flow charts and/or block diagrams as well as combinations of processes and/or blocks in the flow charts and/or block diagrams may be implemented by computer program instructions. The computer program instructions may be provided to a processor of a general-purpose computer, a special-purpose computer, an embedded processing machine, or other programmable data processing devices to produce a machine, such that the instructions executed via the processor of the computer or other programmable data processing devices create an apparatus for implementing the functions specified in one or more processes in the flow charts and/or one or more blocks in the block diagrams.

These computer program instructions may also be stored in a computer-readable memory that can direct a computer or other programmable data processing devices to function in a particular manner, such that the instructions stored in the computer-readable memory produce an article of manufacture including an instruction structure which implements the functions specified in one or more processes in the flow charts and/or one or more blocks in the block diagrams.

The computer program instructions may also be loaded onto a computer or other programmable data processing devices, to cause a series of operational steps to be executed on the computer or other programmable devices, to produce a computer implemented process, such that the instructions executed on the computer or other programmable devices provide steps for implementing the functions specified in one or more processes in the flow charts and/or one or more blocks in the block diagrams.

In a typical configuration, a computing device includes one or more processors (CPU), an input/output interface, a network interface, and an internal memory.

The internal memory may include forms, such as a volatile memory, a random-access memory (RAM), and/or a nonvolatile memory, e.g., a read-only memory (ROM) or a flash RAM, in a computer-readable medium. The internal memory is an example of the computer-readable medium.

The computer-readable medium includes permanent and non-permanent mediums, removable and non-removable mediums, and information storage may be implemented by any method or technology. The information may be a computer-readable instruction, a data structure, a program module, or other data. Examples of the computer storage medium include, but are not limited to, a phase-change random-access memory (PRAM), a static random-access memory (SRAM), a dynamic random-access memory (DRAM), a random-access memory (RAM) of other type, a read-only memory (ROM), an electrically erasable programmable read-only memory (EEPROM), a flash RAM or other internal memory technology, a compact disc read-only memory (CD-ROM), a digital versatile disc (DVD) or other optical storage, a magnetic cassette tape, and a magnetic tape or disk storage or other magnetic storage devices, or any other non-transmission medium, which may be configured to store information accessible to a computing device. As defined herein, the computer-readable medium excludes transitory media, e.g., a modulated data signal or carrier wave.

It should be further noted that the terms such as "comprising", "including" or any other variation thereof are intended to cover non-exclusive inclusions, such that a process, a method, an article, or a device that includes a series of elements not only includes those elements, but also includes other elements that are not explicitly listed, or further includes elements that are inherent to such a process, method, article, or device. An element defined by the wording "comprises a . . . " does not, without more constraints, preclude the existence of other identical elements in the process, the method, the article, or the device that includes the element.

Those skilled in the art should understand that the embodiments of the present disclosure may be provided as a method, a system, or a computer program product. Accordingly, the present disclosure may take the form of an entirely hardware embodiment, an entirely software embodiment, or an embodiment combining software and hardware. Further, the present disclosure may take the form of a computer program product embodied on one or more computer-usable storage mediums (including, but not limited to, a disk memory, a CD-ROM, an optical memory, and the like) having computer-usable program code embodied thereon.

The present disclosure may be described in a general context of computer-executable instructions executed by a computer, e.g., program modules. Generally, the program modules include routines, programs, objects, components, data structures, etc. that execute specific tasks or implement specific abstract data types. The present disclosure may also be practiced in distributed computing environments. In these distributed computing environments, remote processing devices connected through a communication network execute tasks. In a distributed computing environment, the program modules may be located in local and remote computer storage mediums including storage devices.

The embodiments in the present specification are described progressively, identical or similar portions between the embodiments may be mutually referred to, and differences of each embodiment from other embodiments are mainly described in the embodiment. In particular, embodiments of the system are substantially similar to embodiments of the method, and therefore are relatively simply described. A part of description of the embodiments of the method may be referred to for relevant parts.

The above description merely provides embodiments of the present disclosure, and is not intended to limit the present disclosure. For those skilled in the art, the present disclosure may have various modifications and alterations. Any modification, equivalent replacement, improvement, and the like made within the spirit and principles of the present disclosure should be included within the scope of the appended claims of the present disclosure.

What is claimed is:

1. An image-guided method, comprising:
   acquiring a rotation offset, a planned image, and a real-time image of a target object, the rotation offset being generated by a position difference of the target object in a planning stage prior to a treatment stage and a positioning phase of the treatment stage, the planning stage being a stage in which a treatment plan for a patient is formulated; and
   determining a tracking offset based on the rotation offset, the planned image, and the real-time image, the tracking offset being used for tracking the target object.

2. The method according to claim 1, wherein the rotation offset is a positioning rotation offset, and the positioning rotation offset is a rotation offset of the target object determined in a positioning phase.

3. The method according to claim 2, wherein the determining the positioning rotation offset of the target object comprises:
   acquiring the planned image and a positioning image of the target object; and
   determining the positioning rotation offset based on the planned image and the positioning image.

4. The method according to claim 1, wherein the determining the tracking offset based on the rotation offset, the planned image, and the real-time image comprises:
   determining a reconstructed compensation image based on the rotation offset and the planned image; and
   registering the reconstructed compensation image with the real-time image to determine the tracking offset.

5. The method according to claim 4, wherein the determining the reconstructed compensation image based on the rotation offset and the planned image comprises:
   compensating for the planned image based on the rotation offset to obtain a compensated planned image; and
   reconstructing the compensated planned image at a first angle and a second angle respectively, to obtain two reconstructed compensation images corresponding to the first angle and the second angle.

6. The method according to claim 4, wherein the determining the reconstructed compensation image based on the rotation offset and the planned image comprises:
   reconstructing the planned image at the first angle and the second angle respectively, to obtain two reconstructed images corresponding to the first angle and the second angle; and
   compensating for the two reconstructed images corresponding to the first angle and the second angle respectively based on the rotation offset, to obtain two reconstructed compensation images corresponding to the first angle and the second angle.

7. The method according to claim 5, wherein the registering the reconstructed compensation image with the real-time image to determine the tracking offset comprises:
   registering the two reconstructed compensation images with the two real-time images respectively to obtain two first offsets, wherein the two real-time images are obtained by imaging the target object at the first angle and the second angle respectively; and
   computing the tracking offset based on the two first offsets.

8. The method according to claim 6, wherein the registering the reconstructed compensation image with the real-time image to determine the tracking offset comprises:

registering the two reconstructed compensation images with the two real-time images respectively to obtain two first offsets, wherein the two real-time images are obtained by imaging the target object at the first angle and the second angle respectively; and computing the tracking offset based on the two first offsets.

9. The method according to claim 1, wherein the determining the tracking offset based on the rotation offset, the planned image, and the real-time image comprises:

compensating for two real-time images based on the rotation offset to obtain two compensated real-time images, the two real-time images being obtained by imaging the target object at a third angle and a fourth angle respectively;

reconstructing the planned image at the third angle and the fourth angle respectively to obtain two reconstructed images corresponding to the third angle and the fourth angle; and registering the two compensated real-time images with the two reconstructed images to determine the tracking offset.

10. The method according to claim 3, wherein the determining the positioning rotation offset based on the planned image and the positioning image comprises:

reconstructing N positioning images to obtain a three-dimensional image, the N positioning images being obtained by imaging the target object at N different shooting angles respectively, the N being a natural number greater than 2; and registering the three-dimensional image with the planned image to obtain the positioning rotation offset.

11. The method according to claim 3, wherein the determining the positioning rotation offset based on the planned image and the positioning image comprises:

reconstructing the planned image at two orthogonal shooting angles respectively, to obtain two reconstructed images corresponding to the two orthogonal shooting angles;

registering two positioning images with the two reconstructed images to obtain two second offsets, the two positioning images being obtained by imaging the target object at the two orthogonal shooting angles respectively; and computing the positioning rotation offset based on the two second offsets.

12. A radio therapy device, comprising a processor and a memory, the memory storing program instructions, the processor being configured to invoke the program instructions in the memory to execute:

acquiring a rotation offset, a planned image, and a real-time image of a target object, the rotation offset being generated by a position difference of the target object in a planning stage prior to a treatment stage and a positioning phase of the treatment stage, the planning stage being a stage in which a treatment plan for a patient is formulated; and determining a tracking offset based on the rotation offset, the planned image, and the real-time image, the tracking offset being used for tracking the target object.

13. The radio therapy device according to claim 12, wherein the rotation offset is a positioning rotation offset, and the positioning rotation offset is a rotation offset of the target object determined in a positioning phase.

14. The radio therapy device according to claim 13, wherein the determining the positioning rotation offset of the target object comprises:

acquiring the planned image and a positioning image of the target object; and determining the positioning rotation offset based on the planned image and the positioning image.

15. The radio therapy device according to claim 12, wherein the determining the tracking offset based on the rotation offset, the planned image, and the real-time image comprises:

determining a reconstructed compensation image based on the rotation offset and the planned image; and registering the reconstructed compensation image with the real-time image to determine the tracking offset.

16. The radio therapy device according to claim 15, wherein the determining the reconstructed compensation image based on the rotation offset and the planned image comprises:

compensating for the planned image based on the rotation offset to obtain a compensated planned image; and reconstructing the compensated planned image at a first angle and a second angle respectively, to obtain two reconstructed compensation images corresponding to the first angle and the second angle.

17. The radio therapy device according to claim 15, wherein the determining the reconstructed compensation image based on the rotation offset and the planned image comprises:

reconstructing the planned image at the first angle and the second angle respectively, to obtain two reconstructed images corresponding to the first angle and the second angle; and compensating for the two reconstructed images corresponding to the first angle and the second angle respectively based on the rotation offset, to obtain two reconstructed compensation images corresponding to the first angle and the second angle.

18. The radio therapy device according to claim 16, wherein the registering the reconstructed compensation image with the real-time image to determine the tracking offset comprises:

registering the two reconstructed compensation images with the two real-time images respectively to obtain two first offsets, wherein the two real-time images are obtained by imaging the target object at the first angle and the second angle respectively; and computing the tracking offset based on the two first offsets.

19. The radio therapy device according to claim 12, wherein the determining the tracking offset based on the rotation offset, the planned image, and the real-time image comprises:

compensating for two real-time images based on the rotation offset to obtain two compensated real-time images, the two real-time images being obtained by imaging the target object at a third angle and a fourth angle respectively;

reconstructing the planned image at the third angle and the fourth angle respectively to obtain two reconstructed images corresponding to the third angle and the fourth angle; and registering the two compensated real-time images with the two reconstructed images to determine the tracking offset.

20. A non-transitory computer storage medium, storing a computer program, wherein the computer program comprises program instructions, and the program instructions are configured to, when executed by a processor, execute:

acquiring a rotation offset, a planned image, and a real-time image of a target object, the rotation offset being generated by a position difference of the target object in a planning stage prior to a treatment stage and a positioning phase of the treatment stage, the planning stage being a stage in which a treatment plan for a patient is formulated; and determining a tracking offset based on the rotation offset, the planned image, and the real-time image, the tracking offset being used for tracking the target object.

* * * * *